United States Patent
Martin et al.

(10) Patent No.: US 6,526,812 B2
(45) Date of Patent: Mar. 4, 2003

(54) SELF-WASHING INJECTION APPARATUS

(75) Inventors: Werner Martin, Chapel Hill; Thomas Tobien, Durham, both of NC (US)

(73) Assignee: Leap Technologies, Inc., Carrboro, NC (US)

( * ) Notice: Subject to any disclaimer, the term of this patent is extended or adjusted under 35 U.S.C. 154(b) by 0 days.

(21) Appl. No.: 09/907,254

(22) Filed: Jul. 14, 2001

(65) Prior Publication Data

US 2003/0010098 A1 Jan. 16, 2003

(51) Int. Cl.[7] .......................... G01N 13/00; G01N 1/00; G01N 30/02
(52) U.S. Cl. .................. 73/61.55; 73/864.81; 422/70
(58) Field of Search .......................... 73/61.55, 61.56, 73/61.59, 864.86, 864.87, 864.81, 863.72; 436/161; 422/70, 100; 204/600, 647

(56) References Cited

U.S. PATENT DOCUMENTS 3,940,994 A * 3/1976 Klee et al. ................ 73/864.81
4,954,149 A   9/1990 Fullemann
4,967,590 A   11/1990 Miller et al.
5,567,307 A * 10/1996 Karmarkar ............... 210/198.2
5,814,742 A   9/1998 Vissers et al.
6,190,614 B1  2/2001 Fukunaga

FOREIGN PATENT DOCUMENTS

| DE | 3435854 | * | 4/1986 | .......... G01N/30/60 |
| EP | 628813 | * | 8/2000 | .......... B01D/15/08 |
| JP | 10010103 | * | 1/1998 | .......... G01N/30/04 |

* cited by examiner

*Primary Examiner*—Hezron Williams
*Assistant Examiner*—Jay L Politzer
(74) *Attorney, Agent, or Firm*—Kenneth S. Watkins, Jr.

(57) ABSTRACT

Self-washing injection apparatus [101] for liquid chromatography injection valves utilizes an interior chamber [105] with a penetrable seal [109] at the top end of the chamber and a needle sleeve seal [113] at the bottom end of the interior chamber. A wash port [145] in the body [103] of the apparatus connects one or more sources of wash fluid to the interior chamber between the penetrable seal and the sleeve seal. The apparatus provides a simple and effective means to aspirate or pump wash fluids from one or more wash fluid reservoirs through the apparatus, the injection port of the injection valve, and associated components.

14 Claims, 8 Drawing Sheets

SELF-WASHING INJECTION APPARATUS

FIELD OF THE INVENTION

The present invention relates to injection valves for liquid chromatography. In particular, the present invention relates to sample injection apparatus for use with sample injection in injection valves that provides self-cleaning features.

BACKGROUND OF THE INVENTION

A number of advances in high-performance liquid chromatography (HPLC) have reduced required sample volumes, reduced solvent and analyte consumption, improved sample resolution and reduced time and labor required for sampling. One aspect of HPLC testing which remains a problem is sample contamination in the system. In order for testing to be accurate and repeatable, extreme care must be taken to ensure that all parts of the sample equipment in contact with sample fluid are washed or flushed with solvents or wash fluids in order that all possible contamination is removed.

Current methods of sample flushing utilize cleaning the sample injection syringe to remove contaminates. The syringe then provides wash fluid by injection into the sample injection port of the HPLC injection valve. This process must be repeated until all measurable traces of contaminates are removed from the sample equipment.

Injection of wash or solvent fluid into the sample injection port is a time consuming evolution. The process must often be repeated since the volume of the syringe limits the amount of wash fluid injected during each evolution. Multiple injections of wash fluids increase the overall wash time corresponding to a decrease of throughput, and lead to premature wear-out of the movable parts involved.

An improved apparatus and method are needed to wash sample injection valves and associated equipment.

OBJECTS AND SUMMARY OF THE INVENTION

Therefore, an object of the present invention is to provide an apparatus which eliminates the requirement for an injection syringe or canula (probe) connected to a syringe in the sample injection port to wash the inlet portions of the HPLC injection valve.

Another object of the present invention is to provide a self-wash injection apparatus which utilizes separate reservoirs of wash fluids which are transferred by differential pressure to the injection valve of the equipment.

Another object of the present invention is to provide a self-washing injection apparatus for liquid chromatography injection valves that automatically seals the injection port from outside air to allow aspiration or pumping of the wash fluids into the injection valve.

Yet another object of the present invention is to provide a self-washing injection apparatus for liquid chromatography injection valves that reduces labor and the possibilities of errors in liquid chromatography testing.

The self-washing injection apparatus of the present invention attaches and seals to the inlet port of a sample injection valve used in liquid chromatography. The apparatus comprises a body enclosing an interior chamber. A penetrable seal such as a slit seal (duckbill seal) or a septum seal seals the top of the interior chamber. A sleeve seal engageable with an injection needle provides a fluid passageway at the bottom of the interior chamber to the injection port of the injection valve. The length of such a passageway can vary in order to allow positioning of the apparatus either immediately above the injection port of the injection valve or at a position separate from the injection valve. A wash port in the body of the device, connected to the interior chamber between the penetrable seal and the sleeve seal, provides a source of wash fluids during the washing cycle of the apparatus.

During sample injection, a sample injection needle passes through the penetrable seal and the interior chamber of the apparatus and seats in the sleeve seal below the interior chamber. A sealing surface on the ID of the sleeve seal seals the injection needle to the sleeve seal and provides a leak-tight fluid passageway to inject sample fluid into the sample injection valve.

Upon completion of sample introduction, the sample injection needle is removed and the sample injection valve is positioned to provide aspiration to the injection apparatus. The penetrable seal provides an air seal at the top of the interior chamber. The aspiration source draws wash fluids from one or more separate wash fluid reservoirs into the wash port of the apparatus, flushing the interior chamber, the sleeve seal, the injection port of the injection valve, and associated sample components of the sampling system. In other embodiments, a pressure source at the wash fluid reservoir provides the differential pressure to transfer wash fluid from the wash fluid reservoir to the injection port of the injection valve.

In the preferred embodiments, a threaded nipple on the bottom of the apparatus provides an attachment means to the injection port of the injection valve. A ferrule seal seals the apparatus to the injection valve. Multiple wash fluid inlet ports on the outside of the body of the apparatus connect to the interior chamber to simplify connection with one or more wash fluid reservoirs. In other embodiments, the apparatus is mounted remote from the injection valve and a tube connects the apparatus to the injection port of the injection valve.

The self-washing injection apparatus disclosed and claimed herein significantly simplifies washing of liquid chromatography sample components and reduces time and labor required for multiple samples.

BRIEF DESCRIPTION OF THE DRAWINGS

These and other features, aspects and advantages of the present invention will become better understood with regard to the following description, appended claims and accompanying drawings where:

DESCRIPTION OF THE PREFERRED EMBODIMENTS

The following is a description of the preferred embodiments of a self-washing injection port apparatus for use with liquid chromatography injection valves.

Figure 1:
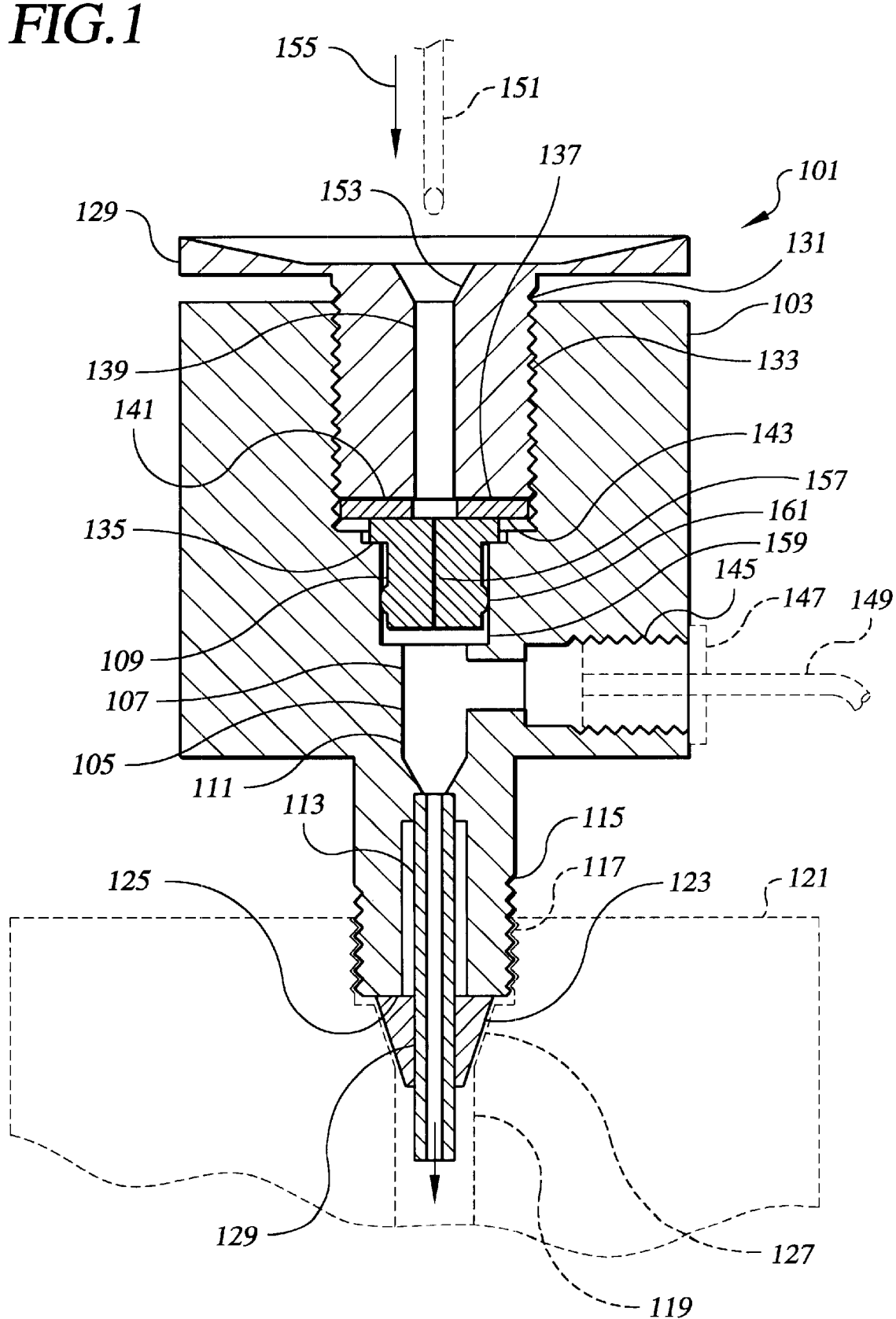
FIG. 1 is a cross section elevation drawing of an embodiment of the self-washing injection apparatus attached to the injection port of a liquid sample injection valve, a sample injection needle positioned above the apparatus for inserting into the needle guide of the apparatus.

FIG. 1 is a cross section drawing of embodiment 101 of the self-washing injection apparatus comprising an injection port body 103 enclosing an interior chamber 105. Penetrable seal 109 seals the upper end portion 107 of chamber 105. A lower end portion 111 of chamber 105 is connected to sleeve seal 113. Threaded nipple portion 115 of injection port apparatus 101 engages matching threads 117 of injection port 119 to secure apparatus 101 to injection valve 121. Ferrule 123 seals apparatus 101 to injection port 119 at bottom seal surface 125 and conical seal surface 127. Tight engagement of threaded portion 115 of the apparatus and matching threads 117 of the injection valve constrict ferrule 123 and seal sleeve seal 113 to the apparatus at seal surface 129.

Top screw 129 retains penetrable seal 109 in seal chamber 159 and compresses penetrable seal 109 by engagement of top screw threads 131 to matching threads 133 of body 103 and seals penetrable seal 109 to chamber 105 at seal surface 135. Teflon washer 137 provides a low-friction engagement between top screw 129 and penetrable seal 109 and seals top screw needle throat 139 at seal surfaces 141 and 143.

Wash port 145 connects to chamber 105 between penetrable seal 109 and sleeve seal 113. Wash port 145 provides a means to circulate wash fluids or solvents through the apparatus as discussed in the following figures. Threaded connector 147 connects and seals wash tubing 149 to wash port 145.

Sample injection needle 151 provides a means of injecting sample fluids into injection port 119 of injection valve 121. Upper needle guide 153 of top screw 129 provides alignment for sample injection needle 151 when inserted into the apparatus in the direction of arrow 155. Slit 157 of penetrable seal 109 provides a resealable passageway for needle 151 when inserted in direction 155. A tight fit between seal 109 and seal chamber 159 at seal bias portion 161 provides a constriction or closing force on slit 157, maintaining a normally-closed seal condition of seal 109. In the preferred embodiments, penetrable seal 109 is made of a resilient material such as rubber or other resilient polymers.

Figure 2:
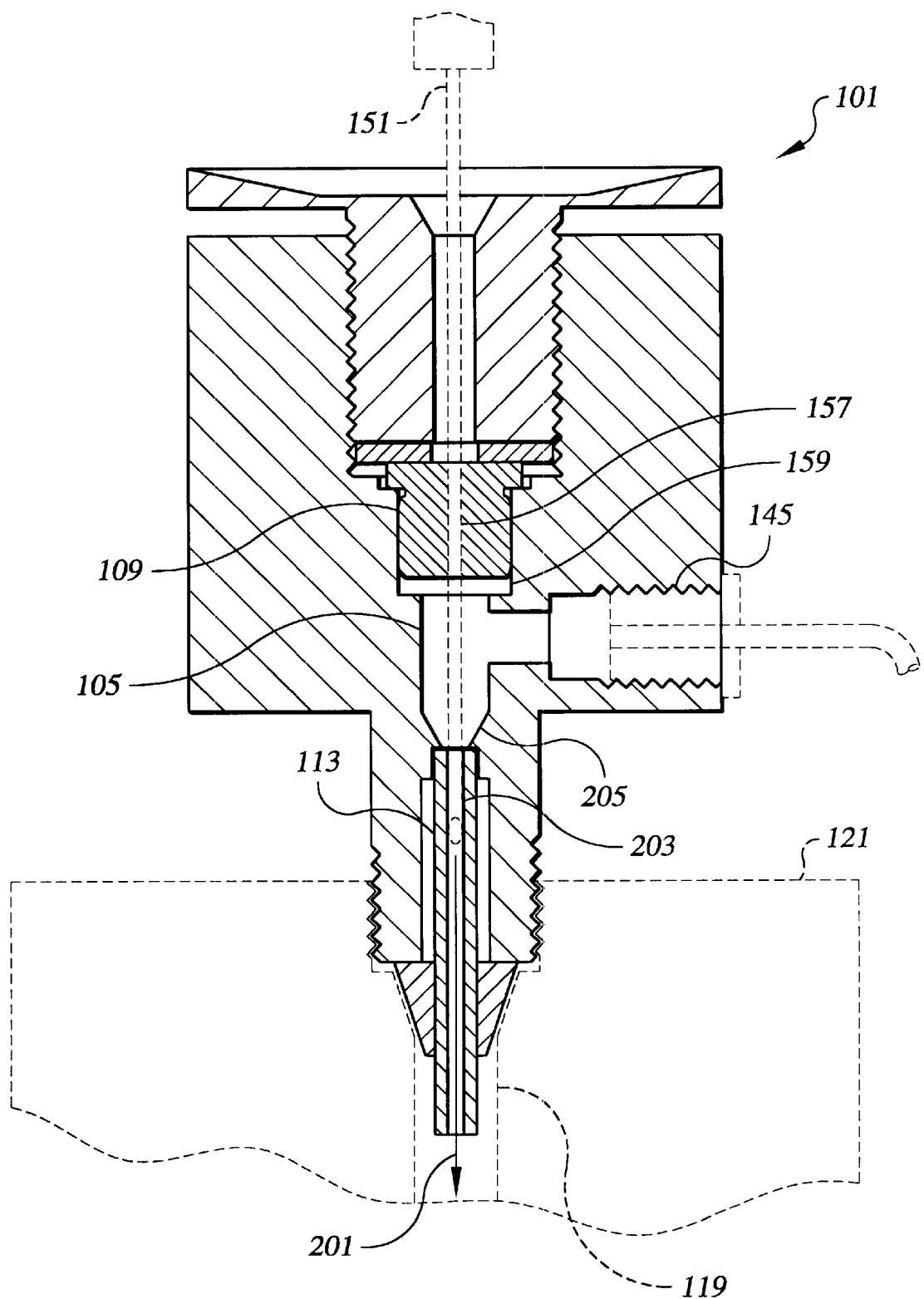
FIG. 2 is a cross section elevation drawing of the injection apparatus of FIG. 1 showing the sample injection needle penetrating the penetrable seal, the interior chamber, and seated into the sleeve seal of the apparatus.

FIG. 2 is a cross section drawing of the injection apparatus 101 of FIG. 1 with injection needle 151 penetrating penetrable seal 109 and seated in sleeve seal 113. In the inserted position, injection needle 151 provides sample injected through the tip of the needle to injection port 119 of injection valve 121 as shown by arrow 201. Interior seal surface 203 of sleeve seal 113 provides a tight fit seal with injection needle 151, sealing injection needle 151 to sleeve seal 113. Lower needle guide 205 provides alignment of needle 151 to sleeve seal 113. Slit 157 of penetrable seal 109 expands when penetrated by injection needle 151 and expands seal 109 against seal chamber 159 as shown in the figure.

Figure 3:
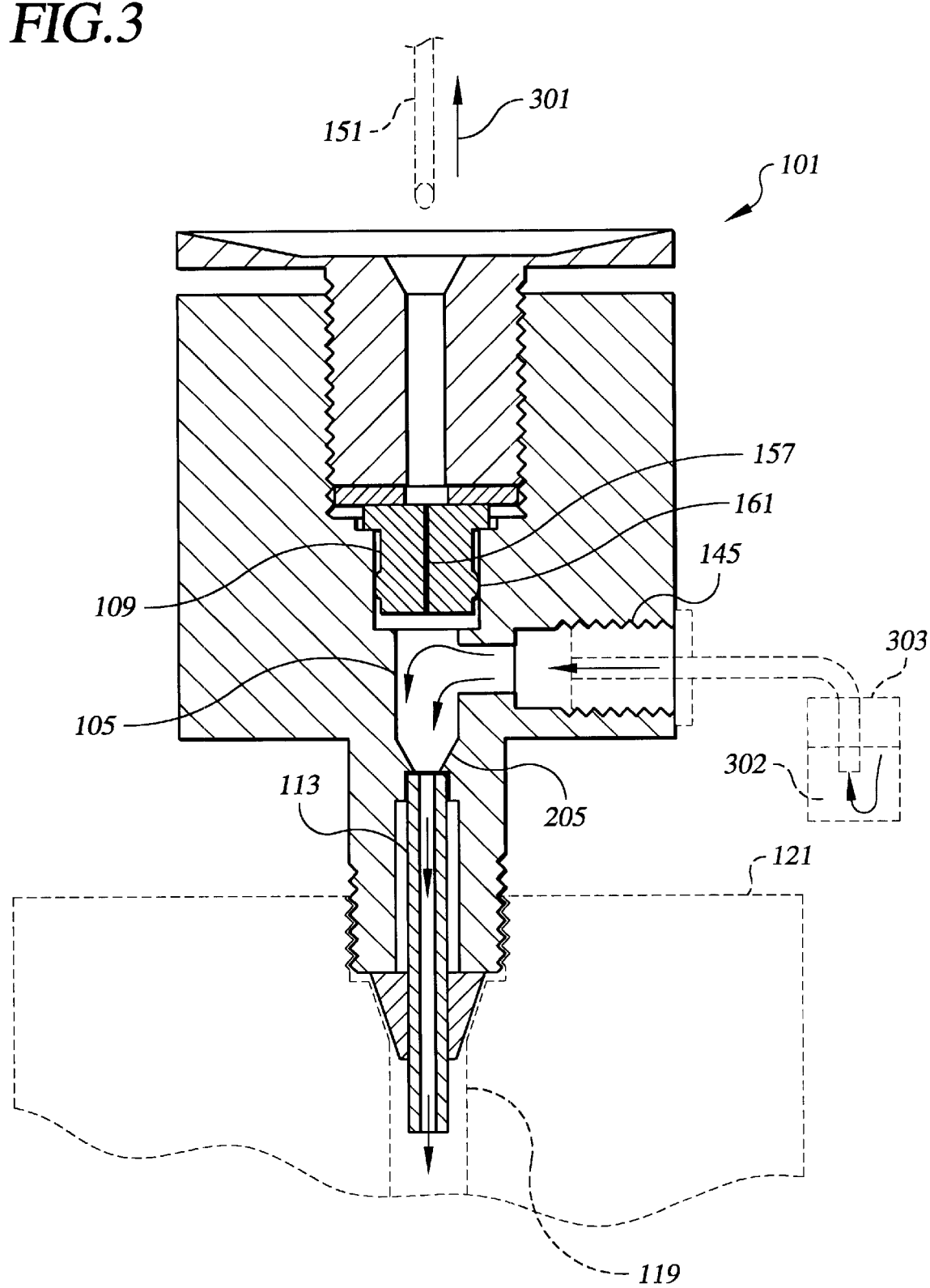
FIG. 3 is a cross section elevation drawing of the injection apparatus of FIG. 1 showing the sample injection needle withdrawn from the apparatus, the penetrable seal in a resealed condition and wash fluid being transferred by differential pressure from a wash fluid reservoir, into the wash port and interior chamber of the apparatus, and out through the sleeve seal of the apparatus, thus allowing washing of the apparatus, the injection port of the injection valve, and associated components.

FIG. 3 is a cross section drawing of the injection apparatus 101 of FIG. 1 with injection needle 151 withdrawn from the apparatus as shown by arrow 301. The resiliency of penetrable seal 109 and the closing bias of bias portion 161 closes and seals slit 157 of penetrable seal 109.

Once needle 151 has been withdrawn from the apparatus, the injection port apparatus and the injection port 119 of injection valve 121 may be washed or flushed utilizing wash port 145. Alignment of injection valve 121 aligns injection port 119 with a suction or aspiration source (not shown). Wash or solvent fluid 302 from wash container 303 is aspirated through the apparatus as shown by the arrows of the figure. Closed slit 157 of penetrable seal 109 prevents air from being aspirated into the apparatus. The apparatus provides thorough flushing of wash port 145, interior chamber 105, lower needle guide 205, sleeve seal 113, injection port 119 of injection valve 121 and associated components of the injection valve.

Figure 4A:
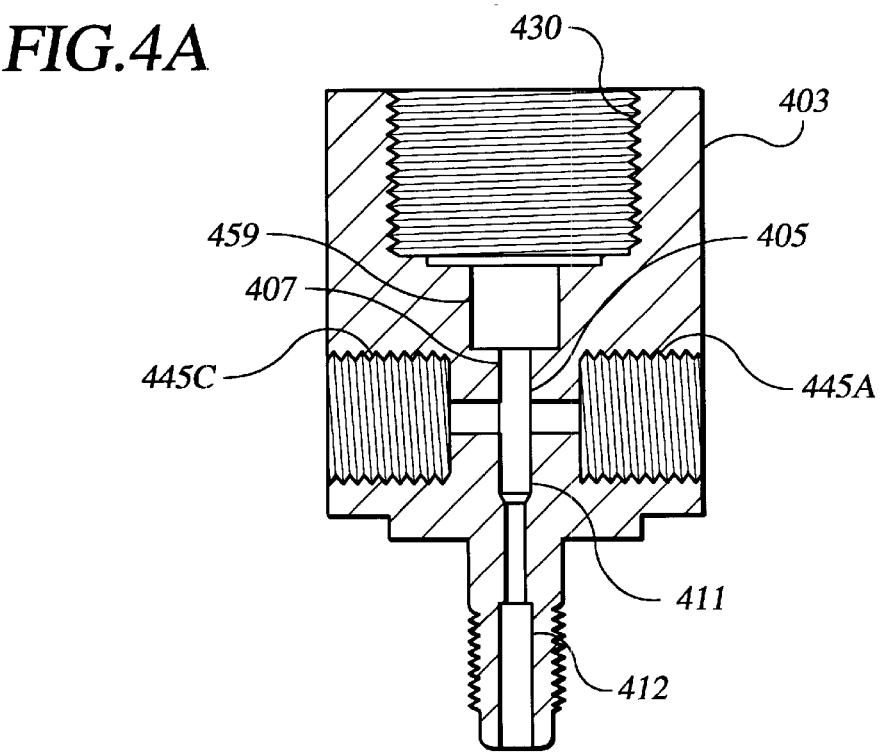
FIG. 4A is a cross section elevation drawing of an alternative embodiment of the injection apparatus body, the body comprising multiply wash ports connected to the interior chamber of the apparatus.

FIG. 4A is a cross section of body 403 of an alternative embodiment of the present invention. In the preferred embodiment, body 403 is machined from round stainless steel bar stock for durability and corrosion resistance. Seal chamber 459 connects to upper end portion 407 of interior chamber 405 and sleeve seal chamber 412 is connected to lower end portion 411 of interior chamber 405.

Wash ports 445A and 445C connect to interior chamber 405 between penetrable seal chamber 459 and sleeve seal chamber 412. In other preferred embodiments, four wash ports (not shown) are connected to interior chamber 105 at quadrants around body 403. Multiple wash ports allow convenient connection of wash fluid connections to body 403 regardless of the orientation of body with respect to adjacent equipment. Unused wash ports are capped with threaded caps.

Figure 4B:
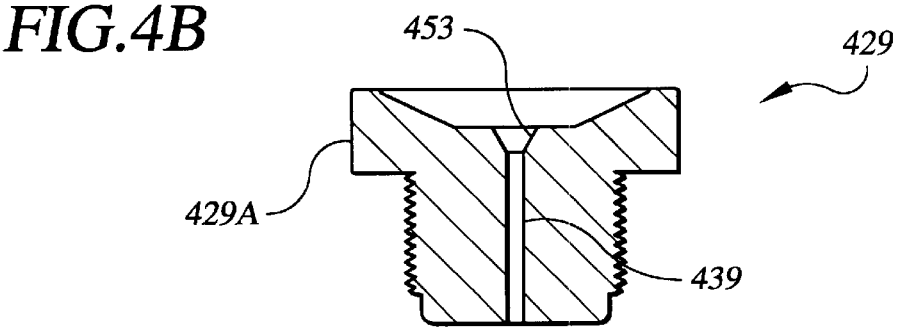
FIG. 4B is a cross section of an alternative embodiment of the top screw of the injection apparatus.
Figure 4C:
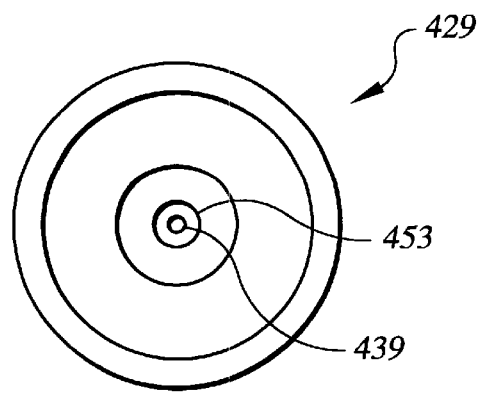
FIG. 4C is a plan view of the top screw of FIG. 4B.

FIG. 4B is a cross section of top screw 429 for threading into top screw chamber 430 of FIG. 4A. In the preferred embodiments, top screw 429 is machined from stainless steel bar stock for durability and corrosion resistance. The outside surface 429A of the upper portion of top screw 429 may be knurled to provide convenient gripping of screw 429 for tightening and un-tightening from body 403. Needle throat 439 provides a through-opening of top screw 429. Upper needle guide 453 provides alignment of a sample injection needle such as needle 151 of FIG. 1. FIG. 4C is a plan view of top screw 429 showing needle guide 453 and needle throat 439.

Figure 5A:
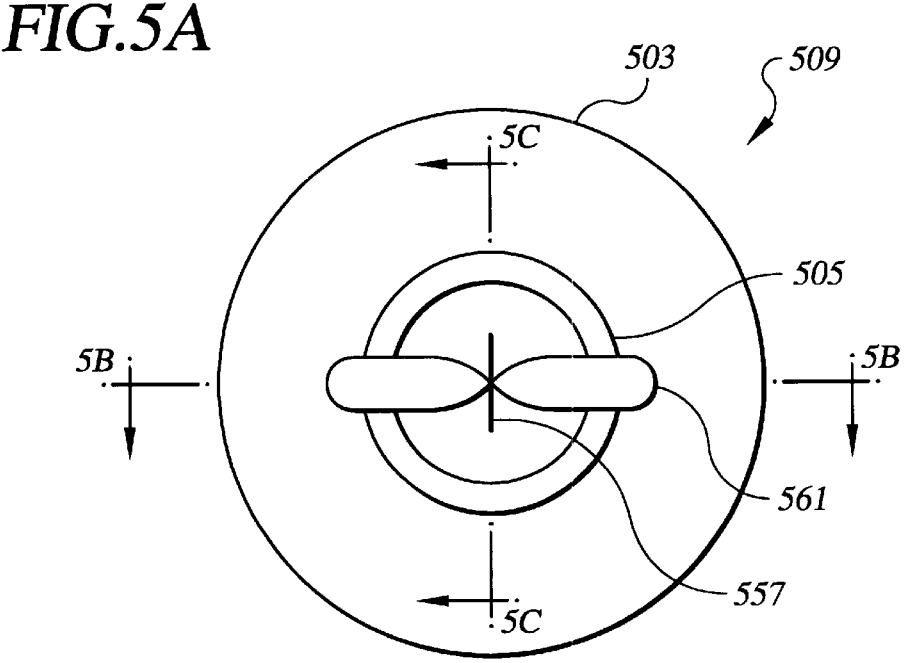
FIG. 5A is a bottom view of a slit-type penetrable seal of the injection apparatus showing bias elements biasing the slit in a sealed condition when inserted into the penetrable seal chamber of the apparatus.
Figure 5B:
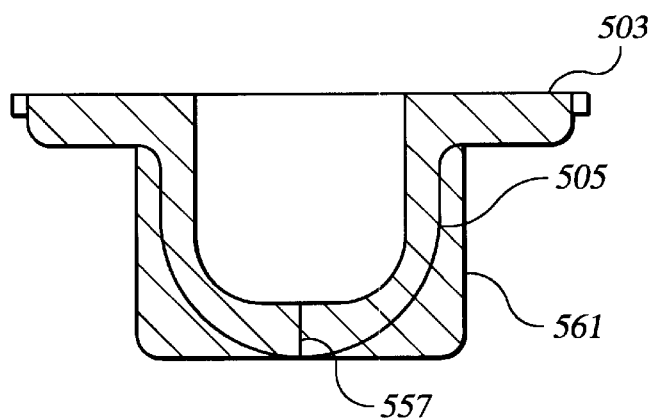
FIG. 5B is a cross section elevation drawing of the slit penetrable seal taken along lines 5B—5B of FIG. 5.
Figure 5C:
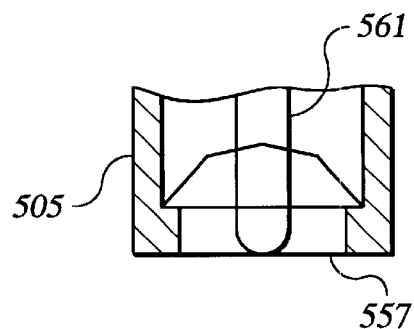
FIG. 5C is a detail cross section drawing of the slit of the seal taken along lines 5C—5C of FIG. 5A.

FIG. 5A is a bottom view of a penetrable seal 509 showing outer support lip 503, seal cup 505, slit 557, and protrusion or seal bias portion 561. FIG. 5B is a cross section elevation drawing of penetrable seal 509 taken along lines 5B—5B of FIG. 5A. FIG. 5C is a partial cross section of the lower cup portion of the penetrable seal taken along lines 5C—5C of FIG. 5A. Seal bias portion 561 extends from seal cup 505 to form an interference fit in a penetrable seal chamber such as chamber 459 of FIG. 4A. The interference fit of bias portion 561 provides a bias closing force on slit 557 so that it remains in a closed, sealed condition unless penetrated by a sample injection needle such as needle 151 of FIG. 2. In other embodiments, the bias closing force is provided by interior protrusions in seal chamber 159.

Figure 6A:
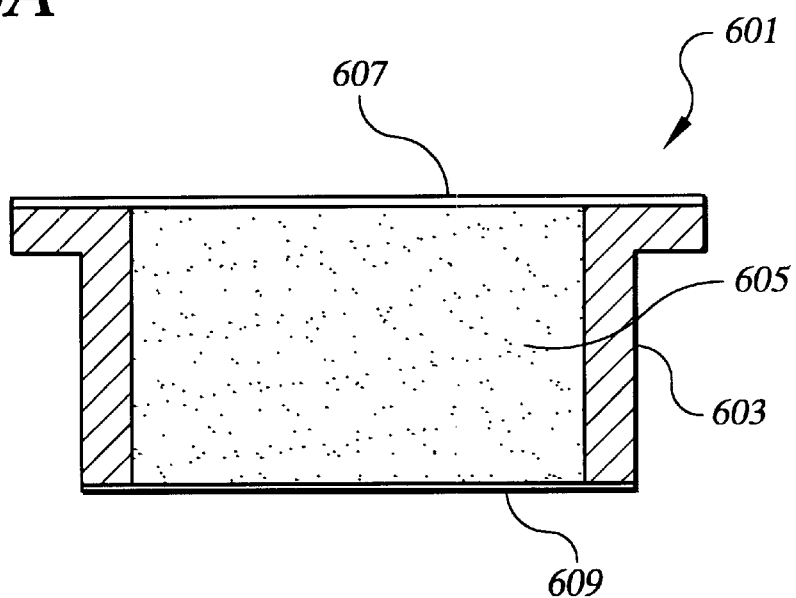
FIG. 6A is a cross section elevation drawing of a septum-type penetrable seal for sealing the upper portion of the interior chamber of the apparatus, the septum seal insertable in the penetrable seal chamber of the apparatus.
Figure 6B:
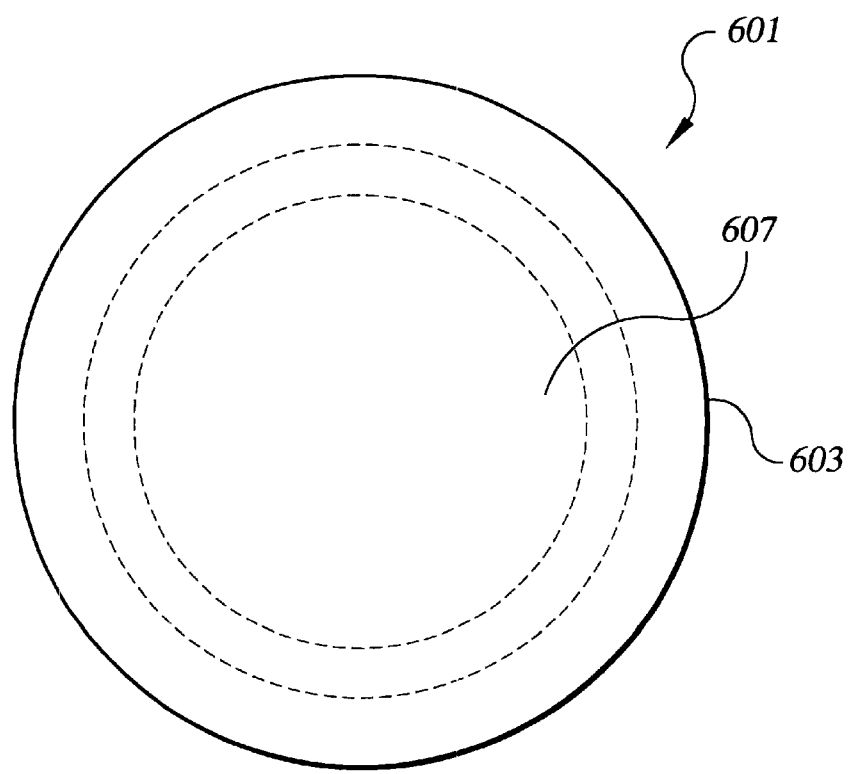
FIG. 6B is a plan view of the septum seal of FIG. 6A.

FIG. 6A is a cross section drawing of another embodiment of a penetrable seal such as septum seal 601. FIG. 6B is a plan view of seal 601. A seal case 603 encloses a sealant 605 such as silicone rubber. In other embodiments, other sealants such as natural rubber, ethylene propylene diene rubber (EPDM), fluorocarbon rubber (FKM), or nitrile rubber (NBR) may be used. Sealant 605 has the property of sealing upon removal of a penetrating needle such as sample injection needle 151 of FIG. 2. An inert film such as PTFE film provides a septum top 607 and a septum bottom 609. In still other embodiments, other septum seals may be used as penetrable seals with an inert film such as PTFE film at either the top or bottom of such septum seals.

Figure 7:
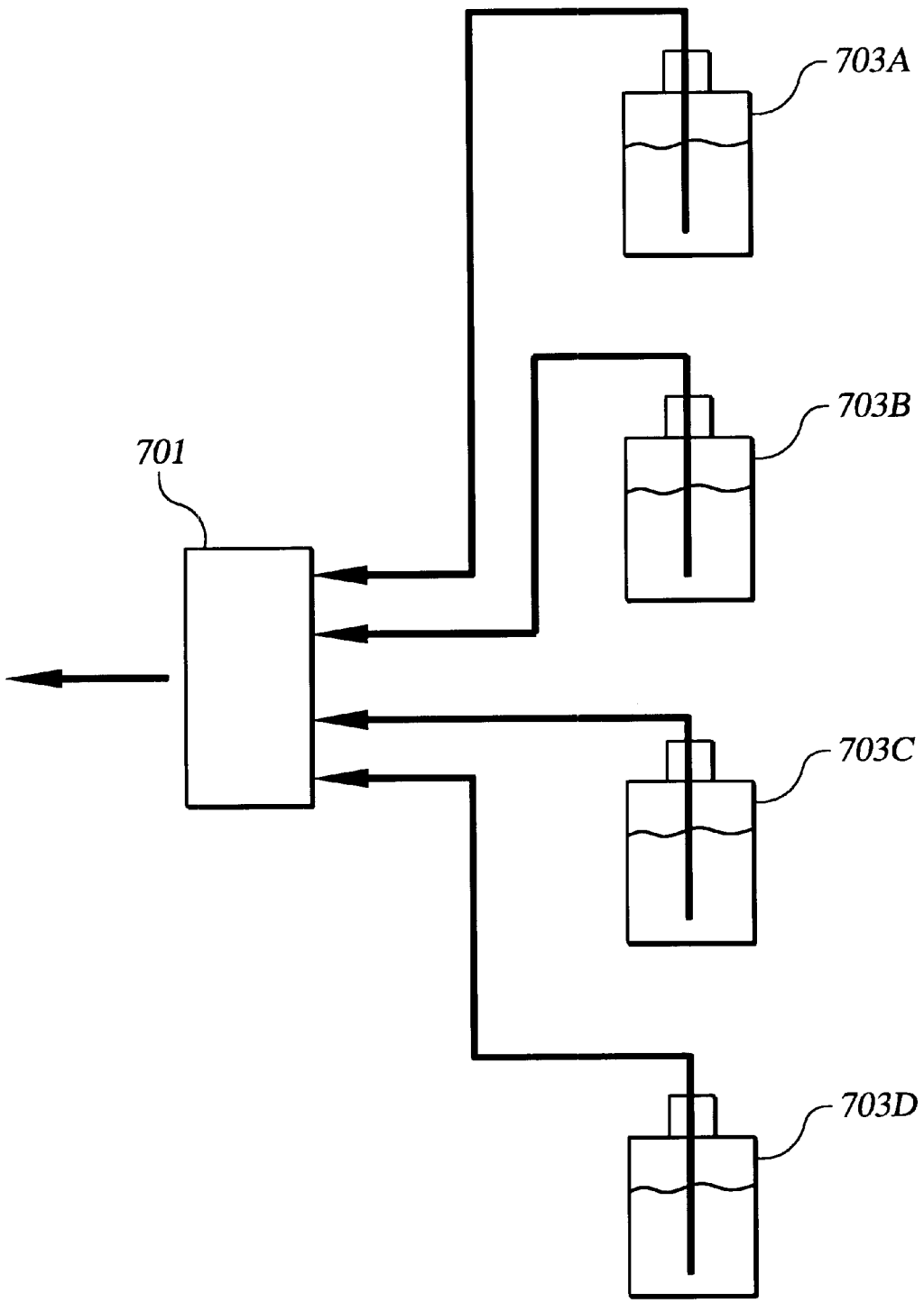
FIG. 7 is a schematic drawing of an embodiment of the present invention utilizing multiple wash fluid reservoirs connected to the wash port of the apparatus by a selection valve.

FIG. 7 is a schematic drawing of an alternative embodiment of the present invention utilizing a selection valve such as multiple port solenoid valve 701 to connect one or more wash fluid reservoirs 703A, 703B, 703C and 703D to the wash port such as wash port 145 of FIG. 1. Wash fluid reservoirs 703A, 703B, 703C and 703D may contain different wash fluids or different solvent concentrations as required by the sampling process. Solenoid valve 701 may be a single-port selection valve, or it may be a mixing-type valve.

Figure 8:
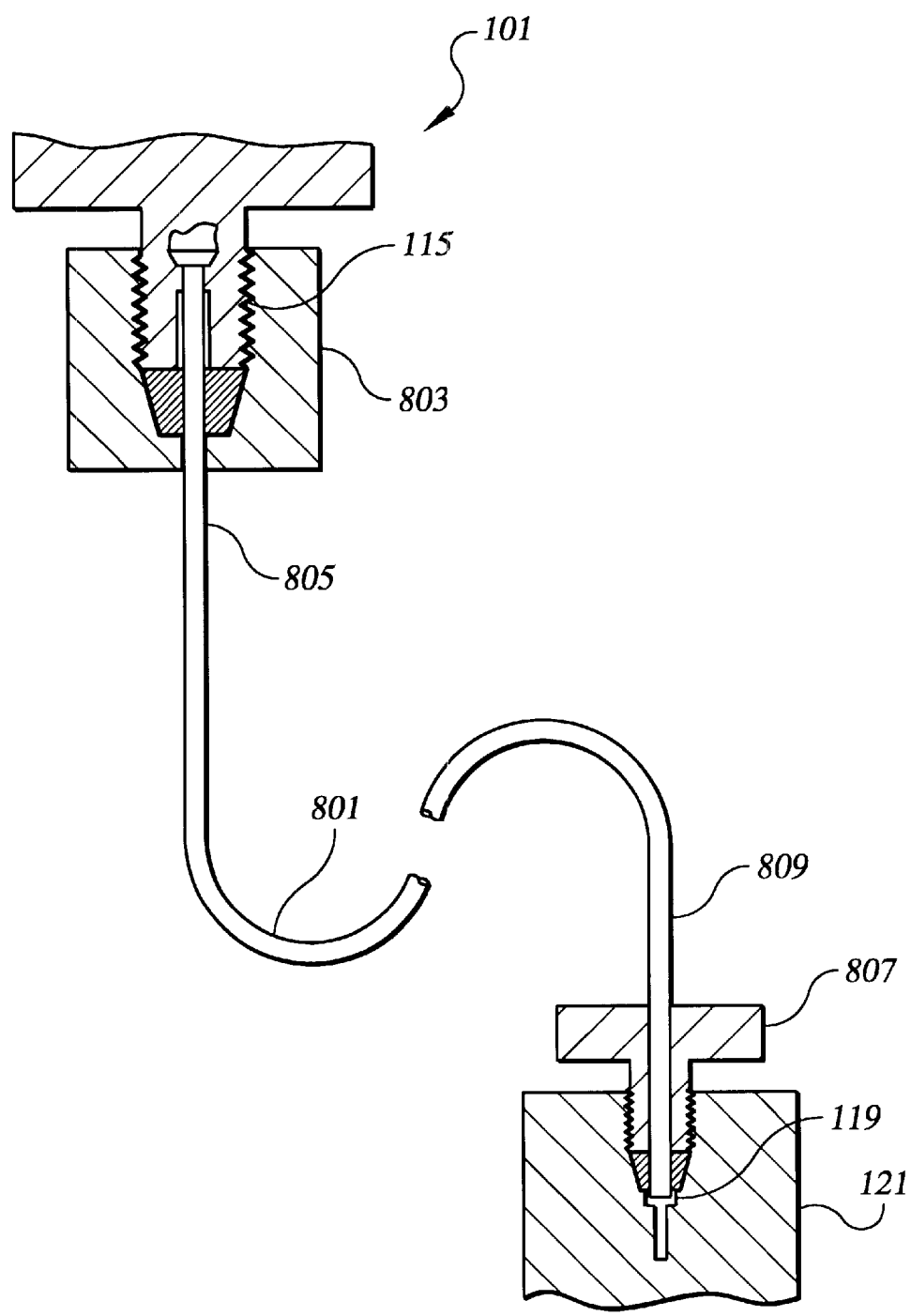
FIG. 8 is a cross-section drawing of an alternative embodiment of the present invention utilizing a connecting tube to connect the injection apparatus to an injection valve to allow remote locating of the injection apparatus.

FIG. 8 is a cross section elevation drawing of an alternative embodiment of the present invention showing an injection apparatus such as injection apparatus 101 of FIG. 1 is attached to the injection port 119 of injection valve 121 by a tube 801.

Threaded female connector 803 seals and connects sleeve seal end portion 805 of tube 801 to threaded nipple 115 of injection apparatus 101. Threaded male connector 807 seals and connects injection valve end portion 809 of tube 801 to injection port 119 of injection valve 121. Tube 801 allows remote location of injection apparatus 101 from injection valve 121. Tube 801 may be a polymeric tube selected as a sleeve seal for injection apparatus 101, or it may be a metal tube such as a stainless steel tube.

Accordingly, the reader will see that the self-washing injection apparatus of the present invention provides an improved apparatus and method for washing fluid sampling liquid chromatography components. The apparatus provides the following additional advantages:

The apparatus eliminates the need to inject wash fluid with a syringe at the injection port of the equipment;

The apparatus improves syringe lifetime by reducing the number of syringe fillings per complete sample injection cycle;

The apparatus improves throughput by allowing simultaneous washing of the sampling syringe and injection valve;

The apparatus reduces labor required for multiple chromatography samples;

The apparatus reduces downtime between multiple chromatography samples;

Existing liquid chromatography auto samplers can easily be retrofitted with the apparatus; and The apparatus is simple and low in cost.

Although the description above contains many specifications, these should not be construed as limiting the scope of the invention but merely providing illustrations of some of the presently preferred embodiments of this invention. For example, the injection apparatus of the present invention may be integrated into an injection valve by threading the body of the apparatus into the inlet port portion of the injection valve. Or, the threaded nipple of the apparatus may be permanently attached to the injection valve, by welding. Thus the scope of the invention should be determined by the appended claims and their legal equivalents, rather than by the examples given.

We claim:

1. A self-washing injection apparatus for use with a liquid chromatography injection valve, the apparatus comprising:
   a body defining an interior chamber;
   a first seal disposed at a first end portion of said interior chamber, said first seal comprising a resilient material penetrable by an injection needle, said resilient material sealing said first end portion upon removal of said injection needle;
   a second seal disposed at a second end portion of said interior chamber, said second seal comprising a needle seal surface sealable with said injection needle;
   a wash port communicating with said interior chamber between said first seal and said second seal; and
   a third seal sealing said apparatus to an injection port of said injection valve.

2. The self-washing injection apparatus of claim 1 wherein said first seal comprises a slit in said resilient material.

3. The self-washing injection apparatus of claim 2 wherein said first seal comprises a bias element biasing the slit in a closed position.

4. The self-washing injection apparatus of claim 3 wherein said resilient material is an elastomer and said bias element comprises a protrusion on an outer diameter of said first seal.

5. The self-washing injection apparatus of claim 1 wherein the first seal is a septum seal.

6. The self-washing injection apparatus of claim 1 comprising a first end, a second end, and a first conical needle guide disposed between said first end and said first seal.

7. The self-washing injection apparatus of claim 6 comprising a second conical needle guide disposed between said first seal and said second seal.

8. The self-washing injection apparatus of claim 1 wherein said second seal is a sleeve seal made of a polymeric material and comprising an inner diameter of predetermined dimensions to engage and seal an outer diameter of said injection needle.

9. The self-washing injection apparatus of claim 7 wherein said third seal comprises a seal element sealing an outer diameter of said sleeve seal.

10. The self-washing injection apparatus of claim 1 wherein said third seal comprises a tube for remotely connecting the apparatus to said injection port to said injection valve.

11. An assembly for liquid chromatography sampling, the assembly comprising:

a liquid chromatography injection valve comprising an injection port connected to a sample injection apparatus, the sample injection apparatus comprising a body defrning an interior chamber;

a first seal disposed at a first end portion of said interior chamber, said first seal comprising a resilient material penetrable by an injection needle, said resilient material sealing said first end portion upon removal of said injection needle;

a second seal disposed at a second end portion of said interior chamber, said second seal comprising a needle seal surface sealable with said injection needle;

a wash port communicating with said interior chamber between said first seal and said second seal; and a third seal sealing said sample injection apparatus to said injection port of said injection valve.

12. A method for washing an injection port of a liquid chromatography injection valve, the method comprising the steps:

attaching a source of wash fluid to a sample injection apparatus comprising a chamber disposed between a first seal and a second seal, the first seal comprising a seal element penetrable by a sample injection needle and resealable upon withdrawal of the sample injection needle, and the second seal comprising a seal surface for sealing an outside diameter of the sample injection needle to the injection port of the injection valve when the sample injection needle is inserted into the second seal;

providing a pressure differential between said source of wash fluid and said injection port of said injection valve; and transferring wash fluid from said source of wash fluid through said injection port of said injection valve.

13. The method of claim 1 wherein multiple sources of wash fluid are attached to the sample injection apparatus.

14. The method of claim 13 wherein a selector valve in line between said multiple sources of wash fluid and said sample injection apparatus selects a current source of wash fluid from said multiple sources of wash fluid.

* * * * *